United States Patent [19]

Feinbloom

[11] Patent Number: 4,498,743
[45] Date of Patent: Feb. 12, 1985

[54] BINOCULAR FIELD OF VIEW SIMULATOR
[75] Inventor: William Feinbloom, New Paltz, N.Y.
[73] Assignee: Designs for Vision, Inc., New York, N.Y.
[21] Appl. No.: 443,489
[22] Filed: Nov. 22, 1982
[51] Int. Cl.³ .............................................. G02C 7/16
[52] U.S. Cl. .............................................. 351/45; 351/46
[58] Field of Search ................ 351/44, 45, 46, 47, 351/48, 115, 118, 128, 201

[56] References Cited

U.S. PATENT DOCUMENTS

| | | | |
|---|---|---|---|
| 1,876,769 | 9/1932 | Sheffield | 351/46 |
| 2,107,102 | 2/1938 | Catron | 351/115 |
| 3,476,466 | 11/1969 | Hopkins | 351/115 |
| 3,873,192 | 3/1975 | Anderson | 351/118 |
| 4,331,393 | 5/1977 | Bradley | 351/138 |

FOREIGN PATENT DOCUMENTS

| | | | |
|---|---|---|---|
| 523937 | 11/1953 | Belgium | 351/46 |
| 4023 | of 1897 | United Kingdom | 351/44 |

Primary Examiner—Rodney B. Bovernick
Attorney, Agent, or Firm—Arthur L. Plevy

[57] ABSTRACT

There is disclosed a simulator for simulating a reduced peripheral field of view for the eyes of a normal user. The simulator consists of a frame having a front section upon which two eye pieces or binocular tubes are mounted. The frame has adjustable temple pieces which are adjustable in the horizontal direction and are adjustable to provide an angle with respect to the vertical so as to adjust the tilt of the frame when it is being worn by the user. Each binocular tube is associated with a variable iris diaphragm which enables the practitioner to adjust the opening to thereby simulate a different field of view according to the particular visual defects associated with a handicapped user. The simulator has left and right shields depending from the temple sections to prevent side vision when the frame is being accommodated by the user. In employing the simulator the device will provide an accurate replica of a reduced field of view such as that existing in a patient having tunnel vision. In this manner the normally sighted can experience the difficulties associated with such visual defects and thereby offer aid and assistance to the handicapped.

16 Claims, 6 Drawing Figures

4,498,743

BINOCULAR FIELD OF VIEW SIMULATOR

BACKGROUND OF INVENTION

This invention relates to an optical simulator and more particularly to a simulator for enabling persons with normal vision to be subjected to a reduced peripheral field of vision. There is a great deal of research being done in the field of optical aids for the visually impaired. Certain eye diseases like Retinitus Pigmentosa Glaucoma and Optical Atrophy, for example, cause the patients to have an extremely reduced peripheral field of view. In extreme cases such diseases can cause tunnel vision. This reduced field of view may exist at the same time that the patient exhibits a good and useful central vision. This is expecially true in Retinitus Pigmentosa.

The above eye diseases cause the persons afflicted to exhibit difficulty in walking and, in general, in navigating. While these diseases can be extremely debilitating, and, essentially the patient must learn to use the limited field of vision to survive and to participate in relatively normal activities. Up to the present, it was desirable to demonstrate this condition of tunnel vision to a relative or friend accompanying the patient to the doctor. In attempting to explain to the relative or friend the condition, the physician used a tube device which had a small aperture. The device was placed in front of one eye to demonstrate the condition. The other eye was blanked out with a suitable cover.

It is, of course, understood that the above technique provided an extremely superficial demonstration of the actual visual handicap. In order to accurately simulate the condition, both for relatives and friends of people so afflicted and for providing further research into the problem, there is a need for an accurate simulator which can reliably simulate the tunnel vision defect to a person having a normal field of vision. It is, therefore, an objective of the present invention to provide a binocular simulator capable of reducing the field of vision of a normal person to enable that person to experience the tunnel vision defect.

BRIEF DESCRIPTION OF THE PREFERRED EMBODIMENT

A binocular field of view simulator for simulating a reduced peripheral field of view for a normal user, comprising a spectacle type frame adapted to be worn by said user. First and second tubular assemblies positioned on the front surface of said frame and each associated with an eye of said user to allow said user to view via said tubular assemblies, and means coupled to said tubular assemblies for selectively adjusting the field of view to thereby simulate a restricted angular field of view as that associated with a visual defect.

DETAILED DESCRIPTION OF THE FIGURES

Figure 1:
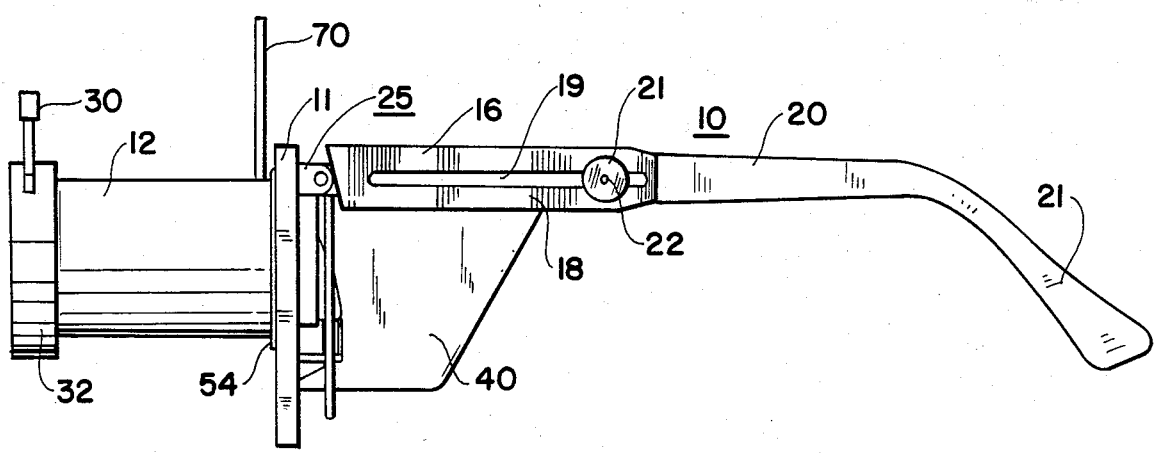
FIG. 1 is a side elevational view of a binocular field simulator according to this invention.
Figure 2:
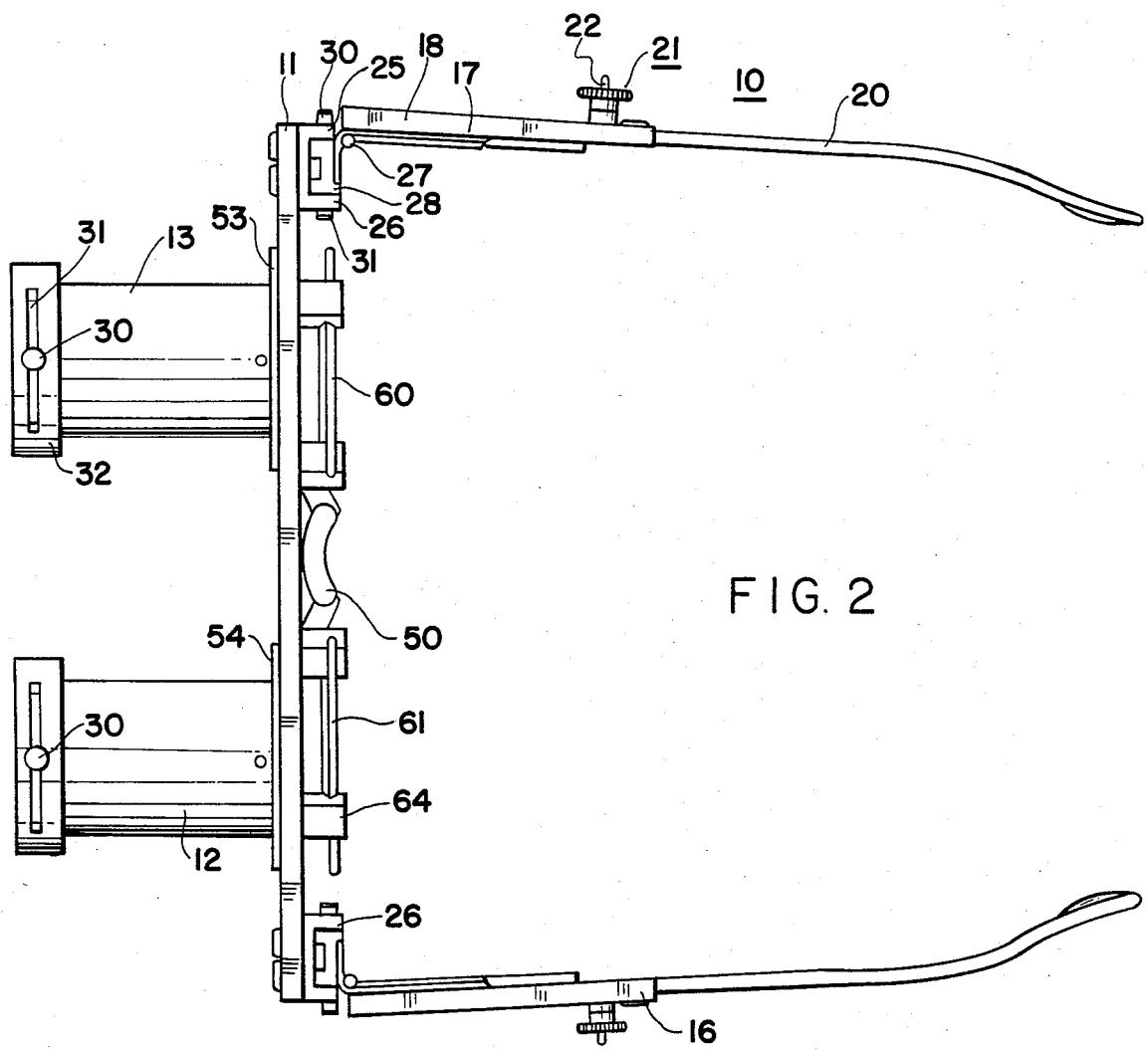
FIG. 2 is a top plan view of the apparatus shown in FIG. 1.
Figure 3:
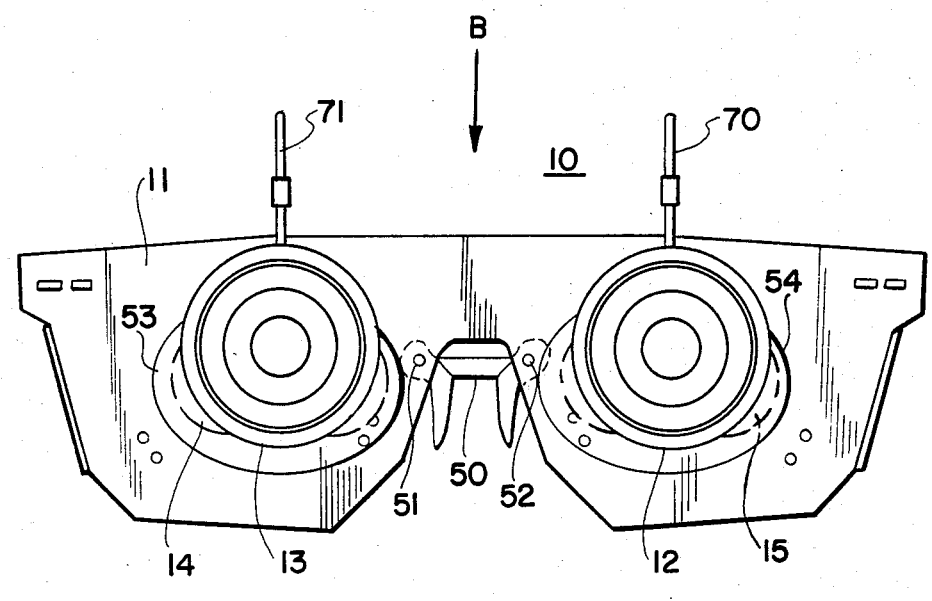
FIG. 3 is a front plan view of the apparatus.

Referring to FIGS. 1, 2, and 3, there is shown respectively a side elevational view, a top view and a front plan view of a binocular simulator 10 according to this invention.

As seen in FIG. 1, the binocular simulator consists of a frame 11 which accommodates two tubes as 12 and 13 mounted and adjustably positioned in special shaped apertures 14 and 15. As will be explained, the apertures allow the optometrist or practioner to adjust the tubes 12 and 13 to the eyes of the person who is accommodating the frame. In this manner, the device can be used to adjust the interpupillary distance between the eyes of a user to enable actual simulation of the particular vision defect. The frame 11 has coupled thereto a right and a left temple members 16 and 17. The temple members are adjustable in the horizontal direction to vary the size according to the dimensions of the user. It is necessary that the temple members be adjustable so that proper alignment of the person's visual axis can be accommodated.

As seen in FIGS. 1 and 2, each temple member consists of two parts. A first part or portion 18 of each temple member has a slot 19 which communicates with an internal hollow of the portion 18. Positioned within the member 18 is an outer member 20 having an ear piece 21 at one end. The members 18 and 20 form a telescopic type of assembly whereby member 20 can be adjusted in the horizontal direction and held in a desired position by means of a set screw 21 and adjustment knob assembly 21. Member 20 has an extending pin 22 which rides in slot 19 of member 18. The adjusting nut, when loosened, will enable the practitioner to vary the length of the temple piece and, when a proper length is achieved, the adjusting nut is tightened to maintain that position. Each temple member as 16 and 18 are coupled to the front section of the frame 11 by means of hinge assemblies as 25 and 26.

As can be seen, the hinge assemblies 25 and 26 allow the temples to pivot so that the physician can adjust the angle of the hinge for accommodating the frame in each individual patient.

As can be seen from FIG. 2, a hinged U-shaped member 26 is secured to the frame assembly. The temple is mounted via a hinge 27 to a central planar member 28 located between the outstanding arms of the U-shaped member 26. Two pivot points 30 and 31 are formed by screws which, when tightened, force the arms of the U-shaped section 26 against the internal surface of the central section 28 to therefore accurately maintain the temple pieces at a desired angle with respect to the front frame section 11. In this manner the physician can tilt the temples at a desired angle with respect to the front frame member 11. Each binocular section as 12 and 13 has a front section which employs an iris diaphragm as of the type found in conventional cameras and so on.

The size of the iris diaphragm is adjusted by means of control rod 30 which is positioned in a slot 31 associated with iris section 32 on the front of the housing. The adjustment of the iris is afforded by the movement of rod 30 so that the actual field of view is varied to enable the physician to demonstrate fields of view as 5 degrees, 10 degrees, and so on. As indicated, iris diaphragms which are completely adjustable are well-known in the art and essentially are analogous to a camera shutter. Diaphragm shutters usually comprise a number of thin plates known as shutter leaves or plates which rotate about pivots so that they open symmetrically in a direct optical axis. It is this type of shutter which constitutes an iris shutter and by movement of the control levers 30, the practitioner is able to adjust the size of the pin hole or to adjust the size of the opening so that he can accurately approximate the given field of view.

Located on each side of the frame as seen in FIG. 1 and depending from each temple, is a side shield as 40. The side shields as 40 appear at both sides of the frame and prevent the patient from side peripheral viewing so that side light and sight is excluded.

Figure 4:
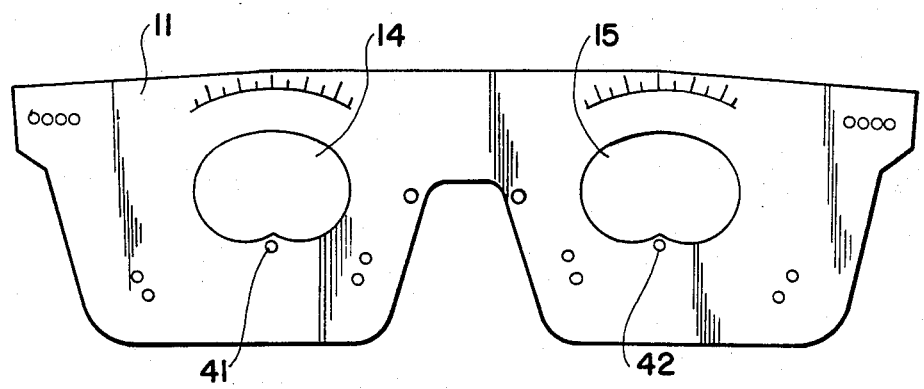
FIG. 4 is a front plan view of the front frame portion without the binocular assembly.

Referring to FIG. 4, there is shown a front view of the frame 11 with the tubes 12 and 13 removed. Each tube has an extending pivot point which rides in apertures 41 and 42 located beneath the openings 14 and 15.

Essentially, the tubes 12 and 13 as mounted in the apertures 14 and 15 and are controlled to determine the correct interpupillary distance for the eyes of the user. The technique employed has been fully described in my coopending patent application entitled, "Adjustable Frame Appartus for Telescopic Spectacles", filed Nov. 28, 1980 as Ser. No. 211,468 and now U.S. Pat. No. 4,364,645, issued on Dec. 21, 1982. In this manner the tube can be tilted or adjusted so that the eyes of the patient can be properly aligned with the center of each tube to simulate the proper field of view.

Referring back to FIG. 2, there is shown a nose piece 50 which is attached to the frame at the conventional location. This nose piece is maintained in position by means of screws in 2 apertures 51 and 52 which hold the nose piece in proper relationship to the front of the frame 11. The apertures accommodate suitable screws and allow various nose pieces to be positioned on the frame to accommodate different size bridges necessary for employment of the frames on various individuals. Also shown in FIG. 2 are two retaining members 60 and 61 which essentially are positioned on the surface opposite the tube and used to accommodate auxiliary trial lenses to enable the physician to insert corrective lenses within the frame necessary to accommodate for the particular prescipion of the user.

Figure 5:
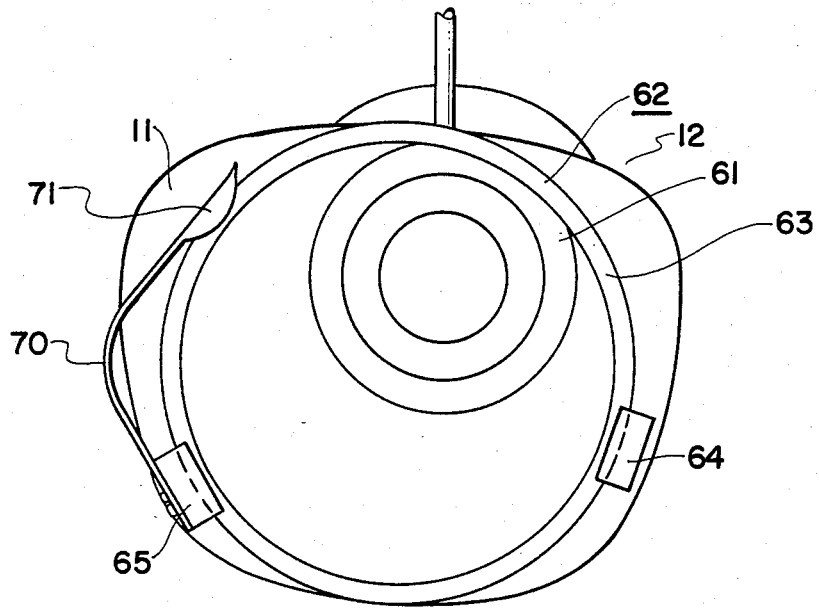
FIG. 5 is a partial view of the rear of the frame assembly showing an auxilary lens retaining structure.

Referring to FIG. 5, there is shown a rear view of a retaining member accommodating a lens 62. Essentially the lens includes an outer rim 63 located on the rear surface of the front of frame 11 is a first clamp member 64 which has a slot for accommodating the rim 63 of the lens. Adjacent member 64 is another member 65 with a similar slot. Secured to member 65 is an arcuate spring member 70 which has a U-shaped top arcuate section 71 which engages the rim 63 of the lens assembly as shown to maintain the lens assembly in proper alignment with the frame 11 and with the optical tube as 12.

As seen in FIGS. 1 and 3, the physician, by moving the tubes within the apertures 14 and 15, employs the extending rods 70 and 71 to rotate the tubes so that proper alignment is afforded. As can be seen from the above description the particular binocular frame assembly depicted affords the following adjustments to the practitioner. The diameter of the iris can be adjusted at each tube so that the physician can simulate a field of view from 5 degrees to 15 degrees. The temples of the frame are completely adjustable both in the horizontal direction due to the telescoping assemblies and also pivotally adjustable due to the pivotal hinge assemblies. Each temple assembly has a corresponding shield which prevents the user from responding to side light and peripheral sight. The simulator also has provision for utilizing various and interchangeable nose pieces to enable different size bridges to be accommodated depending upon the person. The frame depicted has provisions for holding and retaining auxiliary lenses to enable such lenses to correctly compensate for any corrective requirements that the person using the simulator requires.

The above noted simulator thus will enable a practitioner to accommodate a person with a normal field of vision and by utilizing the simulator can actually alter the field of vision to that of a handicapped person having a tunnel vision problem or an extremely narrow field of view. The simulator is extremely useful for providing such aid to handicapped people by allowing those responsible for the person to actually experience the visual defect. The device is further useful for experimental purposes to investigate those problems that are unique to people with limited fields of view. Hence by using this device, researchers have the ability to perform various tasks and then measure their achievement levels utilizing the simulator as described above. The reason that such experiments and investigations are necessary is due to the strict subjective nature of aiding the visually handicapped.

Based on such results, it is known that different individuals require different information in order to respond to the same type of obstacles. Therefore, in using such a device, experiments can determine the type of data or responses which will aid and assist those persons who are severly handicapped by actually allowing the researcher to see as the handicapped person sees.

Figure 6:
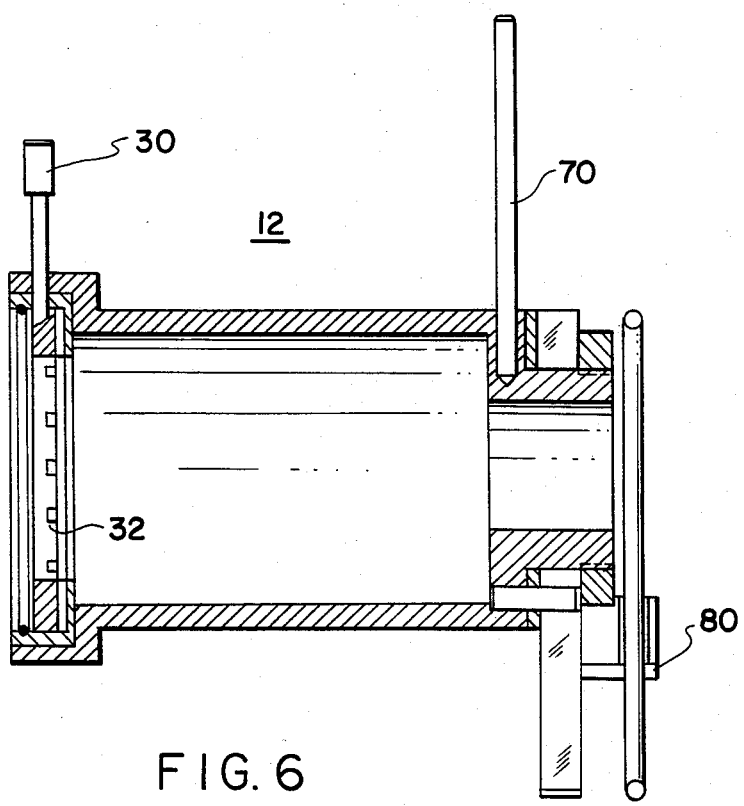
FIG. 6 is a sectional view of a binocular tube.

Referring to FIG. 6, there is shown a sectional view of a typical binocular tube as 12 and 13. Essentially, the length of the tube is approximately 2 inches from end to end with a diameter of 1 inch. As indicated, the tube is positioned within the elongated apertures as 14 and 15 associated with the front of the frame assembly. The rod 70 is used to pivot the tube when the tube is emplaced within the elongated aperture of the frame assembly. The pin 80 is positioned within aperture 41 or 42 to allow the assembly to pivot. As indicated, the rod 30 is used to adjust the diaphragm 32 so that the practitioner can adjust the angle of the field of view to thereby simulate a visual defect associated with a particular handicapped person.

The purpose of the tube is to restrict the sight of the user within the circular area provided by the tube and to thereby allow any light which emanates from the iris to be directed to the normal eyes of the user in a restricted manner thus simulating the tunnel vision effect.

Thus, the simulator essentially allows a person with normal or correctable vision to view as if his field were restricted. The front of the frame 11 is made from a completely opaque material such as metal. In order to prevent vision through the arcuate holes 14 and 15, there is secured an apron 53 and 54 to each tube assembly as 12 and 13 (FIGS. 2 and 3). These aprons 53 and 54 are permanently affixed to the tubes 12 and 13 and operate to block the spaces of apertures 14 and 15 during adjustment of the tubes on the frame assembly. In this manner the user will not be enabled to view through the openings (shown dashed in FIG. 3) indicative of the outer spaces on either side of the tubes 12 and 13 when positioned within the apertures 14 and 15.

I claim:

1. A binolcular field of view simulator for simulating a reduced peripheral field of view for a normal user, comprising:

a spectacle type frame adapted to be worn by said user.

first and second tubular assemblies positioned on the front surface and extending outwardly therefrom of said frame and each associated with an eye of said user to allow said user to view via said tubular assemblies each of said tubular assemblies being cylindrical and of a uniform circular cross section, and means coupled to said tubular assemblies at an end remote from the front surface of said frame for selectively adjusting the field of view between 5 to 15 degrees according to the reduced peripheral field of view simulated to thereby simulate a restricted angular field of view as that associated with a visual defect.

2. The binocular field of view simulator according to claim 1, where said spectacle frame has first and second temple structures each of which is adjustable in length to accommodate different sized users.

3. The binocular field of view simulator according to claim 1, further including retaining means coupled to said tubular assemblies and capable of retaining an auxiliary lens necessary to afford normal vision to said user.

4. The binocular field of view simulator according to claim 1, wherein said means coupled to said tubular assemblies comprises a variable iris diaphragm for selectively providing a variable opening for each of said tubular assemblies to approximate a given angular field of view.

5. The binocular field of view simulator accoding to claim 1 further including shielding means coupled to said spectacle frame and positioned on the left and right sides thereof to block left and right side vision when said frame is being worn by said user.

6. The binocular field of view simulator according to claim 1, wherein said tubular assemblies are adjustably mounted to said spectacle frame.

7. A binocular field of view simulator for simulating a reduced peripheral field of view for a normal vision user to enable said normal user to view a scene according to a predetermined visual defect attributable to a handicapped person, comprising:

a frame adapted to be worn about the head of said user, said frame having a front section positioned in front of the eyes of said user and supported by a bridge overlying the nose of said user, left and right temple members each extending from one side of said frame for coacting with the ears of said user for further supporting said frame, a left and a right tubular member adjustable mounted on said front section with said left tubular member aligned with said left eye and said right tubular member aligned with said right eye, with each tubular member being cylindrical and of a uniform circular cross section with each tubular member extending outwardly from said frame, variable diaphragm means coupled to each tubular member at an end remote from said front section of said frame and operative when varied to provide a predetermined opening for vision via said tubular member and indicative of said reduced peripheral field of view, wherein said variable diaphragm means when varied can provide fields of views between 5 to 15 degrees.

8. The binocular field of view simulator according to claim 7, wherein said front section of said frame has first and second elongated apertures each for receiving one of said tubular members corresponding to said right and left eyes of said user.

9. The binocular field of view simulator according to claim 7, further including pivotable hinge assemblies each for mounting said temple members to said front section for allowing said members to pivot with respect to said front section to adjust the angle of the visual axis of said user.

10. The binocular field of view simulator according to claim 7, wherein said left and right temple assemblies are telescoping assemblies for providing an adjustable length necessary to accommodate different sized users.

11. The binocular field of view simulator according to claim 7, further comprising left and right shielding members depending from said left and right temple members and positioned near said front section for preventing side vision by said user.

12. The binocular field of view simulator according to claim 7, further including auxiliary lens retaining means for each of said tubular members to enable the retention of corrective lenses necessary for providing normal vision to said user.

13. The binocular field of view simulator according to claim 7, including means coupling said front section to said bridge for selectively removing and replacing said bridge according to the size of said user.

14. A method for simulating a reduced peripheral field of view for a normal user having normal vision to simulate a restricted field of view of the type associated with a visual handicapped person, comprising the steps of:

positioning a first tubular member having a uniform circular cross section in front of the right eye of said user positioning a second tubular member having the same uniform circular cross section in front of the left eye of said user emplacing a plate having a predetermined aperture at the front of each tube with said aperture determinative of a given angle manifesting a desired restricted field of view between 5 to 15 degrees.

15. The method according to claim 14, wherein said tubular members are positioned on a frame supported by the head of said user when worn by said user.

16. The method according to claim 14, wherein said plate includes a variable diaphragm for selecting a plurality of different aperture sizes.

\* \* \* \* \*